(12) United States Patent
Mauze et al.

(10) Patent No.: US 6,210,420 B1
(45) Date of Patent: Apr. 3, 2001

(54) APPARATUS AND METHOD FOR EFFICIENT BLOOD SAMPLING WITH LANCET

(75) Inventors: Ganapati R Mauze, Sunnyvale; J. Fleming Dias, Menlo Park, both of CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/233,298

(22) Filed: Jan. 19, 1999

(51) Int. Cl.[7] .................................................. A61B 17/14
(52) U.S. Cl. ............................................. 606/182; 606/181
(58) Field of Search ..................... 606/182, 181, 606/183–185; 600/573, 538, 578, 576

(56) References Cited

U.S. PATENT DOCUMENTS

| | | | |
|---|---|---|---|
| 4,230,118 | 10/1980 | Holman et al. | 128/314 |
| 4,535,769 | 8/1985 | Burns | 128/314 |
| 4,653,513 * | 3/1987 | Dombrowski | 128/765 |
| 4,924,879 | 5/1990 | O'Brien | 128/770 |
| 5,314,442 | 5/1994 | Morita | 606/182 |
| 5,318,584 | 6/1994 | Lange et al. | 606/182 |
| 5,395,387 | 3/1995 | Burns | 606/181 |
| 5,666,966 * | 9/1997 | Horie et al. | 128/760 |
| 5,680,872 * | 10/1997 | Sesekura et al. | 128/760 |
| 5,827,181 | 10/1998 | Dias et al. | 600/322 |
| 5,857,983 * | 1/1999 | Douglas et al. | 600/538 |
| 5,873,887 * | 2/1999 | King et al. | 606/182 |

FOREIGN PATENT DOCUMENTS

| | | | |
|---|---|---|---|
| WO 9637148 * | 11/1996 | (WO) | 600/573 |
| WO 98/24366 | 6/1998 | (WO) | A61B/5/14 |

OTHER PUBLICATIONS

Softclix®, "Lancet Device from the Makers of Accu–Chek® Systems", (Product), PP. (3 pages), Becton Dickinson & Co., Franklin Lakes, New Jersey.

One Touch® Profile™ "Diabetes Tracking System", Owner's Booklet, (Product), PP.31–33, LifeScan Inc.

Glucometer Elite®, "Diabetes Care System", User's Guide, (Product), PP. (3 pages), Miles Inc. Elkhart, IN.

* cited by examiner

*Primary Examiner*—Michael Buiz
*Assistant Examiner*—Lien Ngo

(57) ABSTRACT

A technique for efficiently sampling blood from body tissue by reducing pressure on the body tissue. In the present technique a body tissue is placed under reduced pressure to improve perfusion of blood in the body tissue before lancing. An embodiment of this apparatus includes a lancet carried by a piston slidable in a housing, a mechanism for transmitting mechanical energy internally in the apparatus for creating the reduced pressure on the body tissue. The apparatus also includes a driver that drives the lancet for lancing. The apparatus has a head in the housing for contacting the body tissue in an air-tight manner against suction forces. In the head facing the body tissue is a channel in which the air pressure can be reduced.

24 Claims, 6 Drawing Sheets

APPARATUS AND METHOD FOR EFFICIENT BLOOD SAMPLING WITH LANCET

FIELD OF THE INVENTION

The present invention is related to techniques for lancing skin tissue with a lancet and drawing blood from it and more particularly to apparatuses and methods for lancing skin tissue to obtain an adequate sample with less pain.

BACKGROUND

The analysis and quantification of blood components is an important diagnostic tool for better understanding the physical condition of a patient. Since adequate noninvasive blood analysis technology is not currently available, blood samples still need to be obtained and analyzed by invasive methods from a great number of patients every day. A well known example of such needs is self monitoring of glucose levels by a diabetic individual, often performed in the home of the individual. To obtain a blood sample it is necessary to puncture the skin with a sharp object such as a lancet at a region well supplied with blood vessels, for example, the fingertip. For lancing, a lancet launcher is first loaded with a lancet and cocked by pulling or rotating the cap on the launcher. The tip of the launcher is then pressed against the skin and a button is pressed to launch the lancet to strike the skin.

Currently available lancet launchers are typically pen-shaped devices. The lancet is held in a cylindrical piston which is propelled by a spring mechanism. On cocking, the spring serves to store the energy required to propel the piston forward at the skin. The propulsion of the lancet causes the lancet to impact against and puncture the skin, causing a wound large enough for sampling blood.

Such blood sampling is often painful and inconvenient. As a result, many patients tend to not sample blood as frequently as suggested by the health professionals to monitor the physiological functions adequately. Moreover, for fear of pain in blood sampling, many patients fail to use the lancet launchers properly. Such improper use results in inadequate blood volume being collected and requires repeating the lancing procedure, causing more pain and multiple wounds.

What is needed is a lancet launcher for sampling blood that can be used for sampling blood efficiently, so as to minimize pain to encourage a patient to follow a routine for sampling blood as directed by health professionals.

SUMMARY

In the present invention, the sampling of blood from body tissue is facilitated by applying a negative pressure to the body tissue before and while a lancet is launched to inflict a bleeding wound in the body tissue. This negative pressure is mechanically transmitted internally through substantially the body of the lancet device. In this way, there is no cumbersome suction source attached to the front part of the lancet device to hinder convenient application of the lancet device to the body tissue.

In one aspect, the present invention provides an apparatus having a lancet for sampling blood from body tissue. An embodiment of this apparatus includes a lancet, a housing, and a driver that drives the lancet for lancing. The lancing of the body tissue by the lancet results in a wound for bleeding. The housing is operatively connected to the lancet and shields it before lancing. The housing has a head for contacting the body tissue in an air-tight manner against vacuuming (i.e., suction) forces and having a channel in which the air pressure can be reduced before the lancet is driven to lance the body tissue. As an example, a piston can be included in the channel for air-tight sliding movement against the channel wall along the housing. Mechanical energy is transmitted via the piston from near the rear of the lancet device to near the head to result in reduced air pressure. In one embodiment, a rearward movement of piston in the channel can cause the air pressure in the channel near the head to be reduced before lancing. In another embodiment, withdrawing air through a bore in the piston from the front to the back of the piston while the front of the channel is sealed by the body tissue allows the piston to slide forward to drive the lancet toward the body tissue as the air pressure is reduced at where the lancet device contacts the body tissue.

Currently, finger-prick devices do not provide enough blood for certain tests that require larger volumes. Often large and multiple wounds are required. For example, some patients, such as infants, have veins that are difficult to locate for sampling through an intravenous needle. In these patients the device of the present invention can provide larger volumes for a smaller puncture wound. Also, using the present apparatus, by reducing the environmental pressure on the body tissue to increase its blood perfusion, the depth of penetration by the lancet into the body tissue can be reduced to provide an adequate blood sample. With a smaller penetration depth, the trauma and pain of overpenetration is avoided. Such reduction of discomfort and tissue damage can significantly improve the willingness of patients to comply with, for example, a blood sampling routine. The compact designs of the present lancet devices allow the lancet devices to be conveniently maneuvered without clustering around the lancing location on the body tissue. This is significant for the precise positioning of the lancet device on a desired location on the skin and one-handed operation by a patient who may have lost substantial dexterity due to a chronic illness.

BRIEF DESCRIPTION OF THE DRAWINGS

The following figures are included to better illustrate the embodiments of the apparatus and technique of the present invention. In these figures, like numerals represent like features in the several views.

DETAILED DESCRIPTION OF THE INVENTION

In one aspect, the present invention provides a technique for obtaining an adequate amount of blood by puncturing body tissue while applying a negative pressure to a body tissue to cause bleeding in the body tissue. A bleeding wound can be created by using a lancet. As used herein, a "lancet" is a shaft of any shape having a sharp point or edge for cutting, puncturing, or incising tissue, e.g., by including a blade, pin, needle, or the like.

Figure 1:
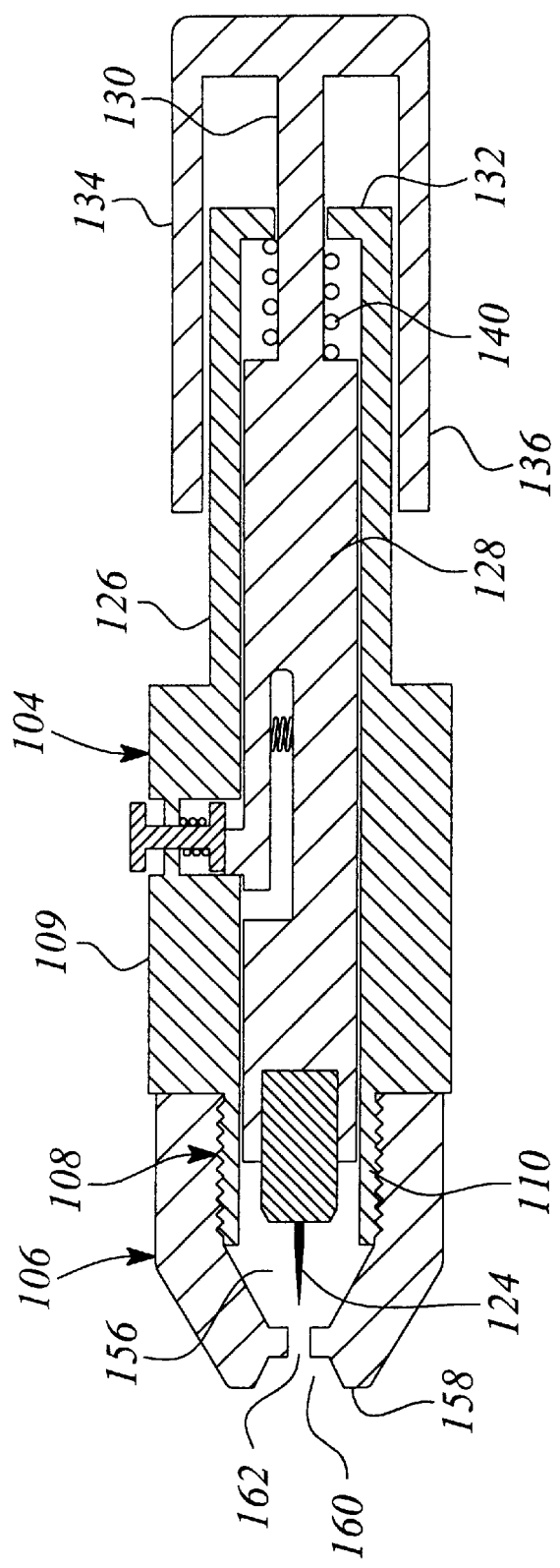
FIG. 1 shows in sectional view an embodiment of an apparatus of the present invention.
Figure 2:
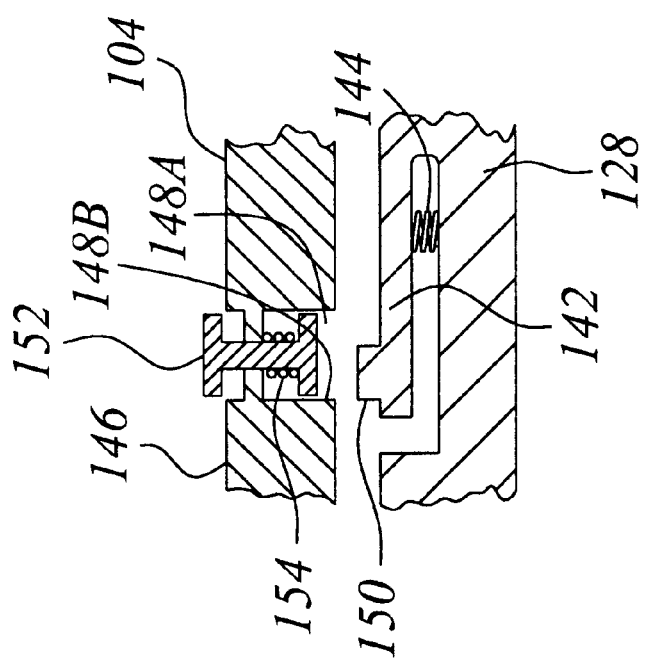
FIG. 2 show an exploded sectional view in portion of the embodiment of the apparatus of FIG. 1.
Figure 2:
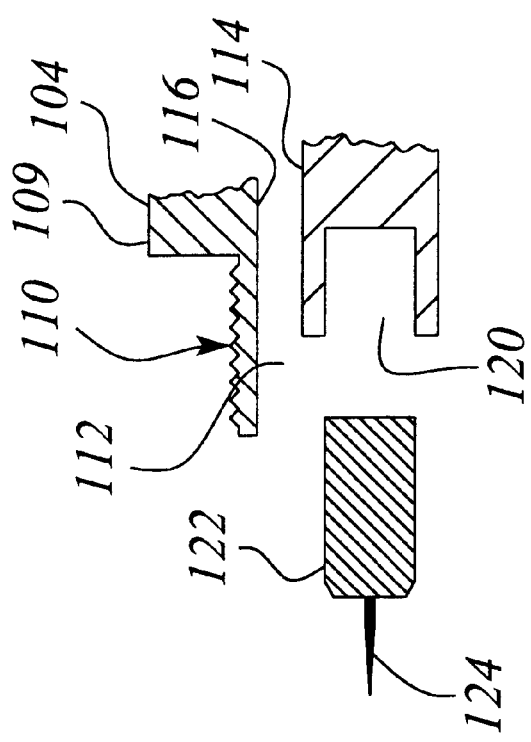

FIG. 1 shows a sectional view of an embodiment of an apparatus for sampling blood from a body tissue (e.g., skin) according to the present invention. FIG. 2 shows an exploded sectional view in portion of the embodiment of FIG. 1. For the sake of clarity of depiction, the lower part of the body 104 (as viewed by the viewer of the figure) is not shown in FIG. 2. In FIG. 1, the apparatus (i.e., lancet launcher) 100 includes a body 104 and a head (or end cap) 106. The head 106 is connected by screw threads 108 to the front part 110 of the body 104 such that by turning the head 106 relative to the body 104, the head 106 can be moved more towards the front or towards the back of the body 104. As used herein, the terms "front," "forward," and "distal" refer to a position or direction that is towards the end where the lancet is. Therefore, these terms ("front, forward, distal," etc.) refer to a position that is near the body tissue to be punctured when the lancet device is applied to lance the body tissue. The terms "back," "rear," "backward," and "proximal" refer to a position or direction that is away from the body tissue to be punctured. The screw threads 108 that connect the head 106 to the body 104 are adequately tight such that air cannot leak through in the normal operation of the device.

As seen in FIG. 1 and FIG. 2, the body 104 has a shell 109 encircling a channel (or lumen) 112 which extends backward from the body's front part 110. A piston 114 can slide against the wall of the channel 112 in an air-tight manner (i.e., there is no substantial leak of air between the cylindrical surface of the piston and the wall of the channel 112 in the shell 109). Preferably the interface between the piston 114 and the channel inside wall (or Luminal wall) 116 is such that there is little friction hindering the sliding motion of the piston in the channel 112. To this end, the piston 114 and the channel inside wall 116 can be made or coated with a low friction material, such as polytetrafluoroethylene. Optionally the interface between the piston 114 and the channel inside wall 116 can be lubricated and sealed against air leak by a liquid lubricant. Low friction materials and lubricants are known in the art and a person skilled in the art will be able to select such materials and lubricants based on the present disclosure.

The distal portion of the piston 114 has a cavity 120 in which a lancet block 122 is snugly secured. The lancet block 122 has a lancet 124 at its distal end. When the piston 114 slides distally forward, the piston 114 pushes the lancet block 122, and therefore the lancet 124, forward to lance the body tissue.

The body 104 of the apparatus, further has a hollow cylinder 126 extending backward and encircling a stem 128 which is rigidly, preferably integrally, connected to the piston 114. The stem 128 has a shaft 130 extending backward and through a back flange 132 to connect to a sleeve cap 134 which has a cylindrical sleeve 136 encircling the shaft 130 and the back portion of the cylinder 126. An actuating spring 140 is positioned between the stem 128 and the back flange 132 such that when the piston is moved backward it causes the stem 128 to compress the actuating spring 140 on the back flange 132. The stem 128 has a cantilever 142 extending distally and is pushed away from the stem 128 towards the channel wall 116 by a spring 144 situated between the cantilever 142 and the stem 128. The mid-portion 146 of the shell 109 has a well 148A. When the piston 114 is moved (or pulled) backward adequately, a finger catch 150 of the cantilever 142 is pushed into the well 148A. When the backwardly pulling force is terminated, the compressed actuating spring 140 urges the stem 128 forward and the finger catch 150 catches on the wall 148B of the well 148A and is retained.

A triggering button 152 is situated in the well 148A above the finger catch 150. Normally the triggering button 152 is urged away from the axis of the channel 112 by a button spring 154. When the triggering button 152 is pushed towards the axis of the channel 112, it dislodges the finger catch 150 from the wall 148B of the well 148A. As a result, the actuating spring 140 drives the stem 128, and therefore the lancet 124, forward towards the body tissue for lancing.

The head 106 also has a channel 156 which is connected to the channel 112 of the body 104 in an air-tight fashion. The head 106 further has a distal ring-shaped ridge 158 encircling a depression 160, which joins by a pore 162 to the proximal portion of the head channel 156. The distal end of the ridge 158 when pressed against the body tissue seals to prevent air leakage such that when the piston 114 is pulled backward the void volume in the head channel 156 is increased, thereby reducing the air pressure therein to a pressure less than that of the ambient pressure, i.e., the air pressure external to the head 106. Due to the reduced pressure, blood perfusion in the body tissue against the depression 160 is increased.

Figure 3:
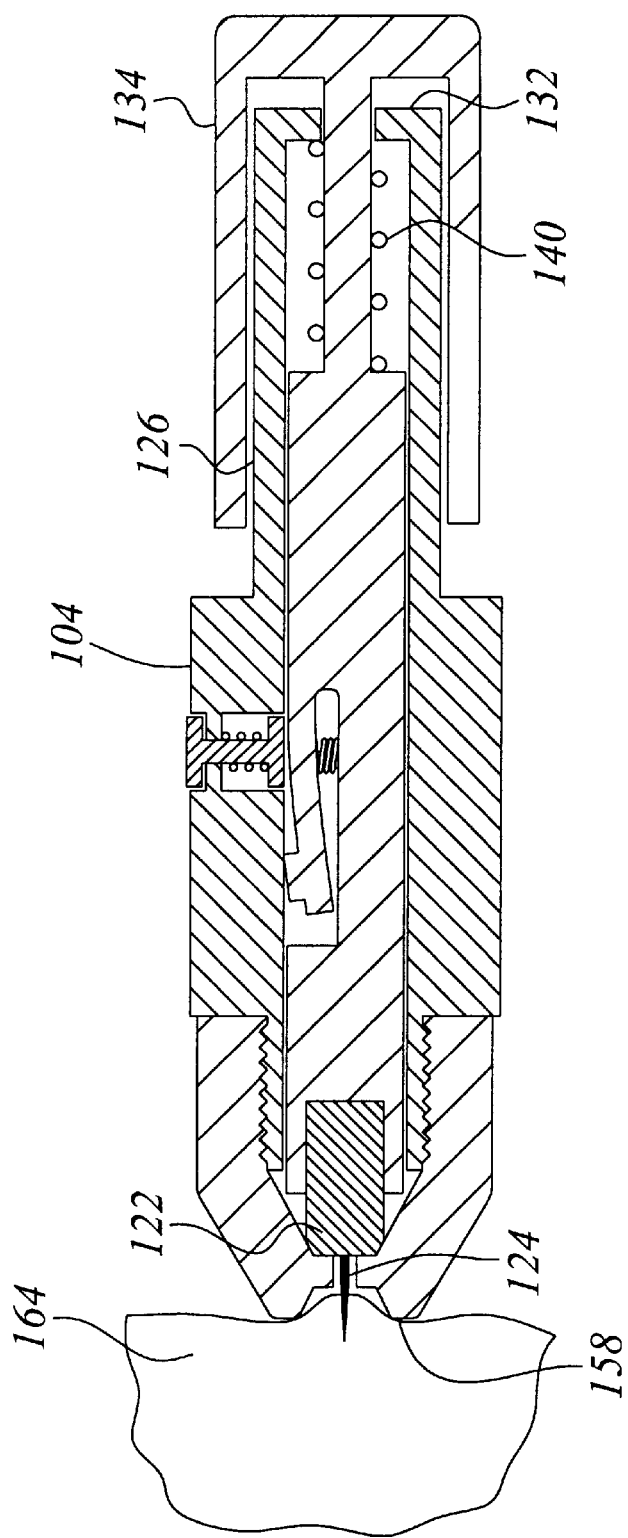
FIG. 3 shows the penetration into a body tissue by a lancet of an embodiment of a lancing apparatus of the present invention.

While the body tissue facing the depression 160 is still under negative pressure (i.e., under a pressure less than that of the ambient pressure), the trigger button 152 is pressed to release the finger catch 150 from the well 148A, thereby driving the lancet forward. Due to its flexibility, when the body tissue 164 is pressed against the ridge 158 the body tissue will extend into the depression 160. Preferably, the depression is made deep enough that it is not necessary for the lancet to extend all the way past the distal end of the ridge 158 for lancing to result in a puncture wound deep enough for blood sampling (see FIG. 3). In this way, the ring-shaped ridge 158 will help to prevent inadvertent injuries to the patient (or user) by an exposed lancet.

Figure 4A:
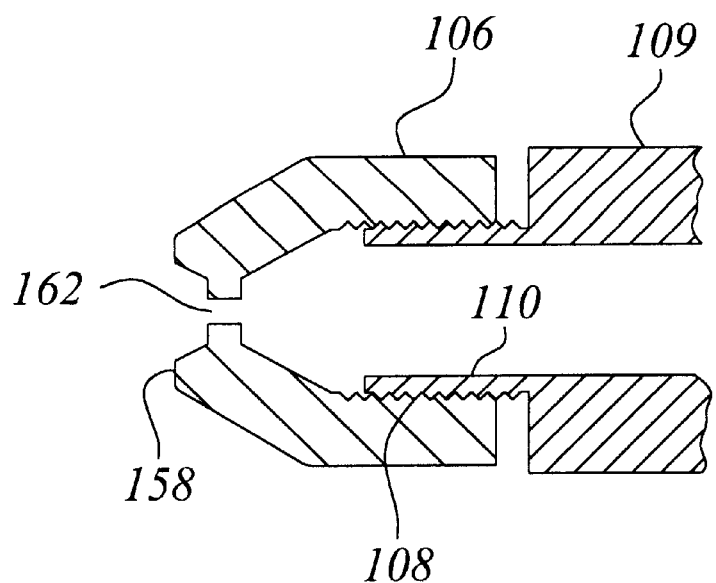
FIG. 4A shows a sectional view in portion of the front part of a lancing apparatus of the present invention.
Figure 4B:
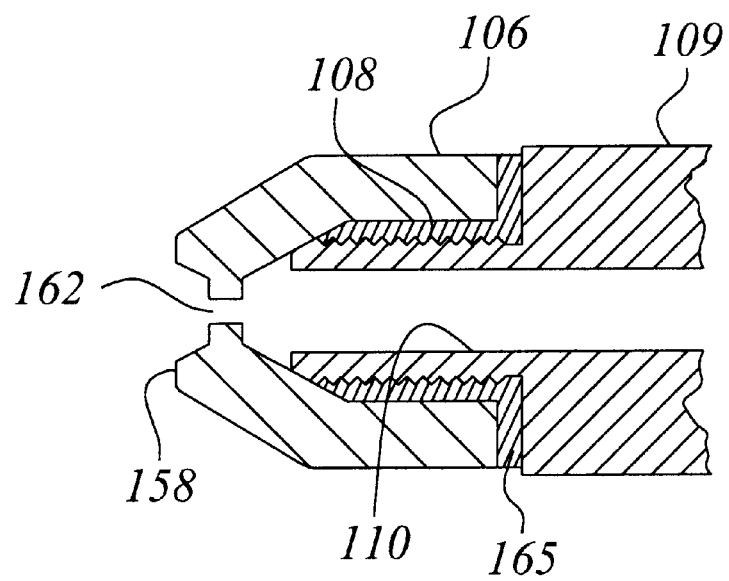
FIG. 4B shows sectional view in portion of the front part of yet another lancing apparatus of the present invention.

Preferably, the head 106 is snugly but detachably connected to the shell 109. As shown in FIG. 4A, the head 106 can be connected by screw-threads with the shell 109 in an air-tight manner. By adjusting the position of the head 106 on the shell 109, the distance that the lancet 124 when launched can extend past the pore 162 can be adjusted. In an apparatus shown in FIG. 4B, the head 106 is held in an air-tight manner by friction on an intermediate sleeve 165, which is threadedly (i.e., by screw-threads) connected to the shell 109. After use, the head 106 can be conveniently detached by pulling from the sleeve 165.

Driving Mechanisms

Figure 5:
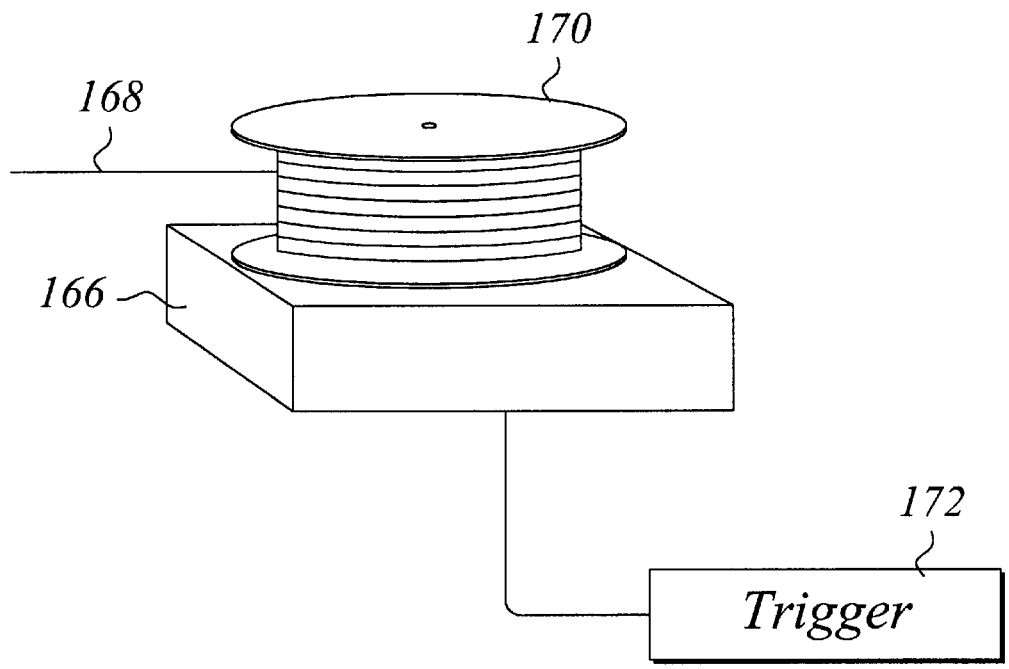
FIG. 5 shows an embodiment of an electrical driving mechanism associated with a lancing apparatus for effecting a reduced pressure on the body tissue.

A wide variety of energy sources can be used for creating the negative pressure and for driving the lancet. The mechanical piston, catch and spring mechanism described above and shown in FIG. 1 is suitable for manual operation by an individual. As an alternative, shown in FIG. 5, the piston 114 (as that of in FIG. 1) can be pulled backward by an electric motor 166 by means of a cord 168 on a spool 170 to cock the stem 128 against the spring 140 (as those of FIG.

1) and create the negative pressure. A trigger 172 can be used to initiate the backward pulling of piston 114 by the motor 166. The motor 166 can either be activated by alternate current or by direct current, such as using batteries. Further, electronics can be included in the lancing apparatus such that once the trigger is actuated, (e.g., after the piston 114 has been pulled back to result in reduced pressure, and an adequate distance has been reached) the piston 114 will be suddenly released and allow the forward driving force (e.g. from the driving spring 140) to launch the lancet forward for lancing. Such electronics can be enclosed, for example, are the motor region or in the housing of the lancing apparatus. Electronics that can perform these functions in within the skill of one skilled in the art.

Figure 6:
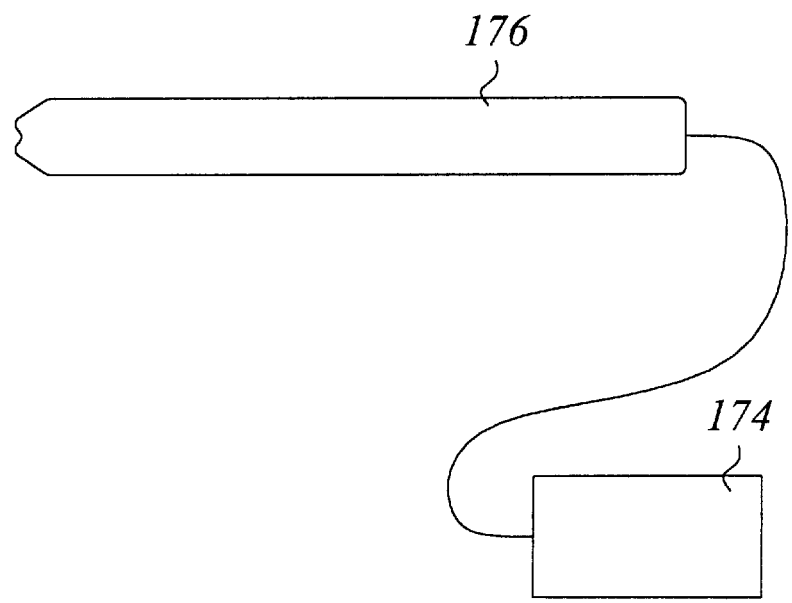
FIG. 6 is a schematic representation that shows an embodiment of an apparatus including an external suction source associated with the lancet launcher.

Furthermore, separate mechanisms can be used for creating the negative pressure and independently for driving the lancet. For example, as illustrated in FIG. 6, a vacuum (or suction) source 174 can be connected to the channel (similar to channel 156 of FIG. 1) of the lancing apparatus 176. With the skin tissue 164 under negative pressure, the lancet can be driven, e.g., by the spring mechanism (similar to spring 140 of FIG. 1) toward to the skin tissue for lancing. Additionally, the lancet can further be driven mechanically, electrically, pneumatically, or hydraulically. Such mechanisms for driving a shaft forward are known in the art and can be adopted to apply in the present lancing technique by one skilled in the art.

Using Vacuum (Suction) for Increasing Perfusion and Driving the Lancet

Figure 7:
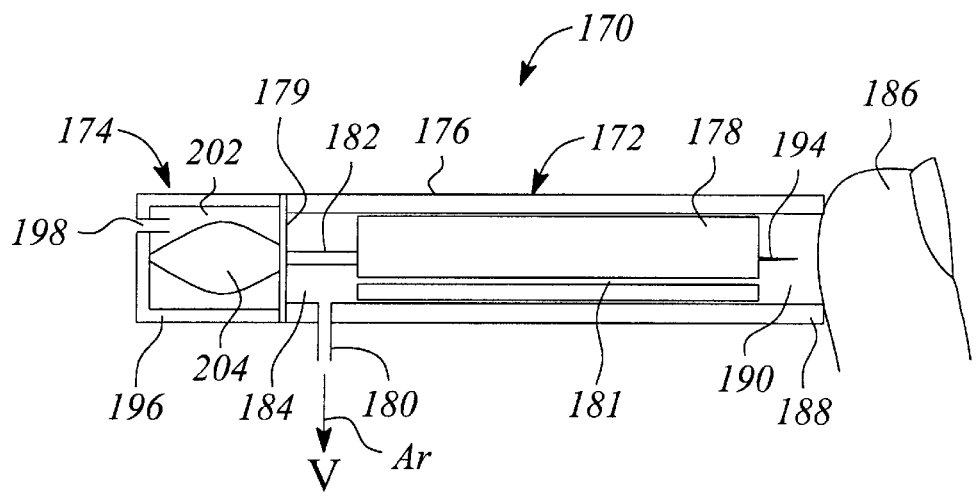
FIG. 7 shows a schematic sectional view of an embodiment with a piston having a bore for transmitting suction.

In another aspect, the present invention provides a technique for using vacuum (i.e., suction) to increase perfusion of a body tissue and drive the lancet to puncture (or incise, cut, etc.) the body tissue simultaneously. FIG. 7 shows an embodiment that has this advantage.

In FIG. 7, a blood sampling apparatus 170 has a body 172 attached to a driver head 174. The body 172 includes a tubular shell 176 in which a piston 178 can freely slide. A flexible diaphragm 179 separates the body 172 and the driver head 174 in an air-tight fashion. A vacuuming port (i.e., suction port) 180 provides access to a suction source (or vacuum source, arrow AR indicates the direction of gas flow to the suction source V). A bore (or passage) 181 in the piston 178 allows air to pass therethrough and the air pressure on the two sides of the piston 178 to equilibrate. The piston 178 is rigidly supported from the diaphragm 179 by rod 182 such that movement of the diaphragm 179 will cause the piston 178 to move. The void area inside the tubular shell 176 between the piston 178 and the diaphragm 179 forms a chamber 184. When a body tissue (such as the flesh of a finger) 186 seals the end 188 of the tubular shell 176 distal from the diaphragm 179, a chamber 190, bordered by the body tissue 186, a distal portion of the shell 176, and the piston 178, results. The piston 178 holds a lancet 194 at an end (the distal end) opposite to the driver head 174.

The driver head 174 has an air-tight cap 196, which has an openable vent 198 to allow air pressure to equilibrate between the atmosphere external to apparatus 170 and a chamber 202 inside the driver head 174. A resilient support 204 (such as compressible object, e.g., a resilient bead or a spring) extends from the diaphragm 179 to the end of the cap 196 on the side of the driver head 174 opposite to the diaphragm 179. The compressible bead can be made with a resilient material such as a polymeric substance. Further, the compressible bead can be solid or a bladder filled with a fluid, such as a gas or a liquid.

Figure 8:
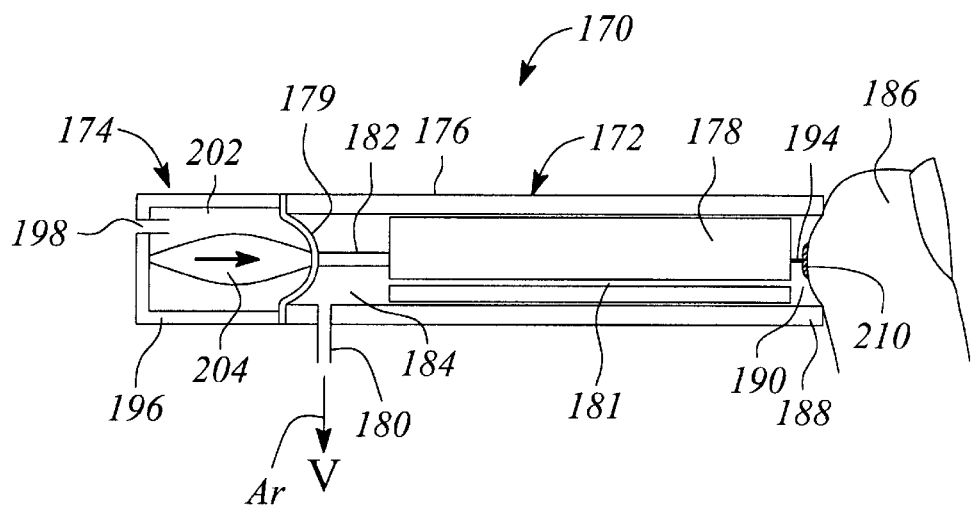
FIG. 8 shows a schematic sectional view of the embodiment of FIG. 7 where the lancet is driven forward.

In operation, as shown in FIG. 8, a suction pulse (can be referred to as a "vacuum pulse") of a predetermined duration and amplitude is applied to the suction port 180. The negative pressure is transmitted to the chamber 184, and through the bore 181 to the chamber 190. The negative pressure in the chamber 184 causes the diaphragm 179 to flex forward (i.e., towards the lancet 194), thereby extending the resilient support 204. This forward extension of the diaphragm 179 causes the piston 178 to move a finite distance. The negative pressure communicated through the bore 181 to the chamber 190 causes the tissue to be sucked against the forward end 188 of the tubular shell 176 and increases the blood flow to that tissue. The simultaneous movement of the advancing lancet and the suction on the tissue against the tubular shell 176 drives the needle 194 to puncture the tissue of the finger 186, thereby causing bleeding from the puncture wound. Thus, blood 210 is emitted from the lancing wound and is sampled from the finger tissue by the application of suction. The suction source provides the driving force for driving the lancet 194, as well as providing the reduced environmental pressure on the tissue to increase blood flow and bleeding. The removal of the suction restores the piston 178 to its original position of FIG. 7.

Although preferred embodiments of the present invention have been described and illustrated in detail, it is to be understood that a person skilled in the art can make modifications within the scope of the invention.

What is claimed is:

1. An apparatus for sampling blood from body tissue, comprising:
    (a) a lancet for lancing the body tissue to result in a wound for bleeding;
    (b) a housing operatively connected to the lancet and shielding the lancet before lancing, the housing having an internal channel and a head for contacting the body tissue in an air-tight manner against suction forces, the housing having a piston which has sliding motion along the housing when implementing suction at the head in the reduction of air pressure at the body tissue prior to lancing the body tissue to create a wound; and
    (c) a driver for driving the lancet toward the body tissue for lancing while the body tissue is under suction.

2. The apparatus according to claim 1 wherein the piston has a channel along its length, the housing has a rear portion remote from the lancet and wherein air passes through the channel of the piston from the head to about the rear portion as the air pressure at the head is being reduced, wherein the piston has a surface in slidable contact with the housing in an air-tight manner.

3. The apparatus according to claim 1 wherein the piston is slidably housed in the channel for air-tight sliding movement in the channel against the housing in a direction away from the head to reduce air pressure at the head.

4. The apparatus according to claim 1 wherein the head has a depression and a pore connected together, the depression being more towards the front of the head than the pore, both the depression and the pore being at the front portion of the channel.

5. The apparatus according to claim 4 wherein the head has a ridge encircling the depression for sealing against the body tissue.

6. The apparatus according to claim 5 wherein the lancet will extend to protrude forward through the pore in the head when driven for lancing, the protrusion of the lancet being not more forward than the ridge to reduce the risk of inadvertent injury to a user.

7. The apparatus according to claim 5 wherein the lancet protrudes forward through the pore into the depression when driven to lance, and wherein the head is adjustably secured in the housing to adjust the protrusion into the depression.

8. The apparatus according to claim 3 wherein the driver includes a spring which is compressed when the piston is moved to reduce air pressure in the channel, the spring can be decompressed thereafter to urge the lancet toward the body tissue.

9. The apparatus according to claim 8 wherein the housing further comprises a catch for operatively holding the piston to maintain the spring in a compressed state, wherein releasing the piston from the catch will permit the decompression of the spring to drive the lancet forward.

10. The apparatus according to claim 3 wherein the driver further includes a means for moving the piston backward to reduce air pressure in the channel before the piston is driven forward for lancing.

11. The apparatus according to claim 2 wherein the piston carries the lancet and has an open bore internally extending longitudinally from proximate to the head to proximate to the rear portion allowing air to pass through to a suction source at the rear portion to reduce pressure in the channel at the head, thereby sliding the piston forward by suction.

12. The apparatus according to claim 11 further comprising a resilient support for allowing the piston to be pulled forward by a reduction in air pressure at the head and retracting the piston when the reduction in air pressure is removed.

13. A method for sampling blood from a body tissue, comprising the steps of:
   (a) providing a lancing device which has a lancet for lancing and has a head with an opening for receiving blood from sampling and further having a housing with a channel in the lancing device extending longitudinally therein, the housing having a slidable piston therein, the piston carrying the lancet;
   (b) applying the head with the opening against the body tissue and reducing air pressure in the channel at the head and on the body tissue to a pressure less than the ambient pressure while slidably moving the piston along the housing away from the head; and
   (c) after step (b), puncturing the body tissue with the lancet.

14. The method according to claim 13 further comprising sliding the piston in the channel away from the head to generate a reduced pressure at the head when the head is applied against the body tissue, the piston carrying the lancet for lancing.

15. The method according to claim 13 further comprising applying a head having a ridge encircling a depression to seal the ridge against the body tissue against air leakage before reducing air pressure in the channel.

16. The method according to claim 15 further comprising extending the lancet to protrude forward through the opening into the depression for lancing and limiting the protrusion of the lancet to no more forward than the ridge to reduce the risk of inadvertent injury to a user.

17. The method according to claim 13 further comprising extending a lancet forward through the opening into the depression for lancing and adjusting the limit of extension of the lancet before extending the lancet.

18. The method according to claim 13 wherein the channel includes a head channel connected to a body channel and the method further comprises moving the piston backward in the body channel to reduce the air pressure in the head channel and compressing a spring at the same time, the spring can be later decompressed to urge the lancet toward the body tissue.

19. The method according to claim 13 further comprising moving the piston backward and retaining it against the driving force of a spring to result in reduced air pressure in the channel at the head, and thereafter releasing the piston to allow the piston to be driven forward by the spring for lancing.

20. A method for sampling blood from a body tissue, comprising the steps of:
   (a) providing a lancing device which has a lancet for lancing and has a head with an opening for receiving blood from sampling and further having a housing with a channel in the lancing device extending longitudinally therein, the housing having a piston disposed in the channel;
   (b) applying the head with the opening against the body tissue and reducing air pressure in the channel at the head and on the body tissue to a pressure less than the ambient pressure, wherein the step of reducing air pressure in the channel at the head and on the body tissue comprises the substep of sucking air through a passage extending longitudinally through the piston from the head to a suction source proximate to a portion of the lancing device remote from the head to effect a reduced pressure in the channel at the head, the piston being slidable in the lancet device and carrying the lancet such that the reduced pressure at the head causes the piston to slide towards the body tissue for lancing; and
   (c) after step (b), puncturing the body tissue with the lancet.

21. A method for inserting a lancet through the body tissue of a patient, comprising the steps of:
   (a) providing a lancing device having a housing and a lancet carried by a slidable piston therein, the housing having a head and a channel extending longitudinally in the housing and leading to an opening in the head, the head for the lancet to extend therein for lancing, the opening having a ridge encircling a depression for receiving blood;
   (b) applying the housing with the ridge against the body tissue, such that the body tissue reaches into the depression;
   (c) reducing the air pressure on the body tissue to a pressure less than the ambient pressure by one of mechanically drawing air and sliding the piston from the head to a rear portion of the housing through the channel, wherein the air pressure on the body tissue is being reduced while the piston is sliding along the housing;
   (d) after the step (c) of reducing the air pressure on the body tissue, puncturing the body tissue with the lancet by extending the lancet in the channel forward in the opening to not pass the end of the ridge; and
   (e) receiving blood into the depression from the body tissue.

22. An apparatus for sampling blood from body tissue, comprising:
   (a) a lancet for lancing the body tissue to result in a wound for bleeding;
   (b) a housing operatively connected to the lancet and shielding the lancet before and during lancing, the housing having an internal channel and a head for contacting the body tissue in an air-tight manner against suction forces, the housing having a piston which can be slid in the housing in a direction away from the head to implement suction at the head on the body tissue in the reduction of air pressure at the body tissue prior to lancing the body tissue to create a wound; and (c) a driver for driving the piston to push the lancet toward the body tissue for lancing while the body tissue is under suction, the lancet not extending beyond the head during lancing.

23. An apparatus for sampling blood from body tissue, comprising:

(a) a lancet for lancing the body tissue to result in a wound for bleeding;

(b) a housing operatively connected to the lancet and shielding the lancet before lancing, the housing having an internal channel and a head for contacting the body tissue in an air-tight manner against suction forces, the housing having a piston which has sliding motion along the housing when implementing suction at the head in the reduction of air pressure at the body tissue prior to lancing the body tissue to create a wound, the piston being in rigid relation to the lancet and has a channel extending longitudinally from proximate to the head to proximate to the rear portion allowing air to pass from the head through the piston to a suction source at the rear portion to reduce pressure in the channel at the head, thereby sliding the piston towards the head by suction from the suction source; and (c) a suction source for moving the lancet toward the body tissue for lancing while the body tissue is under suction.

24. The apparatus according to claim 1, wherein the piston slides along the housing while reduces air pressure on the body tissue by one of expanding air space of air above the body tissue and allowing air to pass through the piston to a suction source.

* * * * *